United States Patent [19]

van Valkenburg et al.

[11] 4,056,971
[45] Nov. 8, 1977

[54] DISTANCE AMPLITUDE COMPENSATION SYSTEM

[75] Inventors: Howard E. van Valkenburg, New Fairfield; Vincent P. McCarroll, Monroe, both of Conn.

[73] Assignee: Automation Industries, Inc., Los Angeles, Calif.

[21] Appl. No.: 684,679

[22] Filed: May 10, 1976

[51] Int. Cl.² ............................................. G01N 29/04
[52] U.S. Cl. ....................................................... 73/629
[58] Field of Search ................... 73/67.7, 67.8 R, 67.9

[56] References Cited

U.S. PATENT DOCUMENTS

| | | | |
|---|---|---|---|
| 3,033,029 | 5/1962 | Weighart | 73/67.8 R |
| 3,260,105 | 7/1966 | McNulty | 73/67.9 |
| 3,872,715 | 3/1975 | Pittaro | 73/67.9 |
| 3,972,228 | 8/1976 | Mansson | 73/67.7 |

*Primary Examiner*—Charles A. Ruehl
*Attorney, Agent, or Firm*—Thomas L. Flattery

[57] ABSTRACT

A distance amplitude compensation system is disclosed herein for comparing received signals with a reference signal having a time varying amplitude. The preferred embodiment of the invention disclosed herein is particularly adapted for use in an ultrasonic nondestructive testing system to vary the reference signal of the system as a function of time to compensate for variations of the echo signal produced by changes in the amplitude of the ultrasonic energy as it propagates through the workpiece as a result of attenuation or other causes. A pulser/receiver transmits ultrasonic signals into the workpiece, receives echo signals returned therefrom and produces received signals corresponding to the echo signals. A distance amplitude compensation generator produces a reference signal that has an amplitude that varies with time as a function of the manner in which the ultrasonic energy changtes as it propagates through the workpiece. The reference signal and the received signals are applied to a comparator circuit and if any of the received signals are larger than the reference signal a threshold train of pulses is transmitted to an alarm coincidence AND gate circuit which is gated for a predetermined period of time to produce an alarm if a flaw is detected in the workpiece. The alarm coincidence circuit may be coupled to any suitable utilization device such as a pulse counter to signal a flaw in the workpiece. The reference signal and the received signal are also applied to a suitable display device such as a CRT which has unblanking circuitry coupled thereto to unblank the CRT at predetermined periods of time to provide a display of the reference signal and the received signals.

17 Claims, 16 Drawing Figures

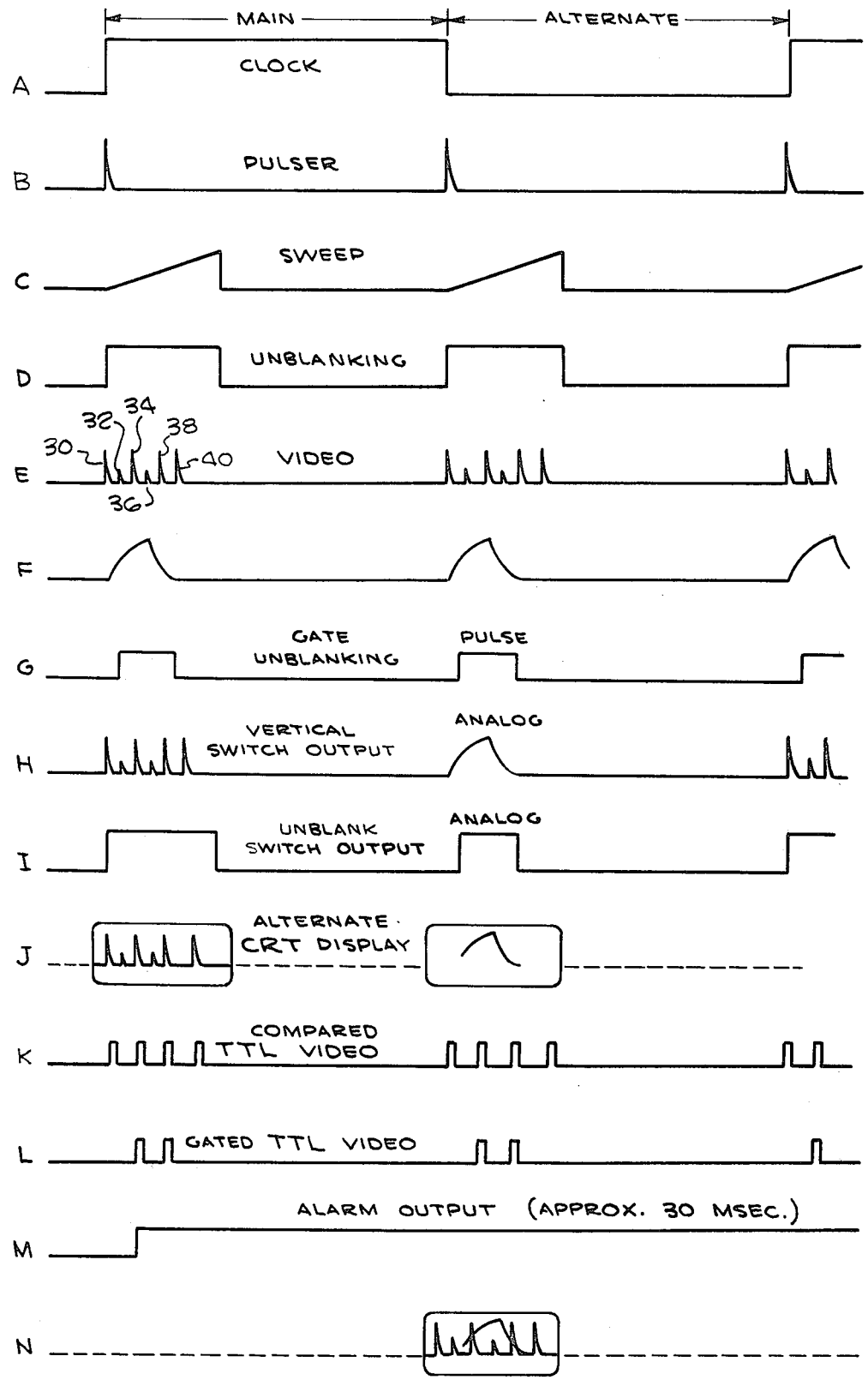

DISTANCE AMPLITUDE COMPENSATION SYSTEM

BACKGROUND

The present invention relates to a distance amplitude compensation system and more particularly to a system for providing a reference signal that has an amplitude that varies as a function of time.

The use of ultrasonic pulse echo techniques to test workpieces has been long known. Such techniques typically provide for the periodic generation of high frequency electric pulses and applying them to a piezoelectric element which transforms the electric vibrations into mechanical vibrations which are then transmitted into the object under test. The transmitted pulses are reflected from the rear boundary of the workpiece as well as from any internal discontinuities in the workpiece such as cracks, inclusions and flaws. The presence of such defects can therefore be determined by detecting the reception of pulses reflected by the piezoelectric element which transforms the detected mechanical pulse vibrations into electric voltage signals. The electric signals may be processed to be viewed on a cathode ray tube or other similar utilization device to determine flaws in the workpiece.

The magnitude of signals detected which indicate flaws would be ordinarily a function of the size of the defects. However, the signal is also a function of the distance of the defect in the workpiece below the entering surface of the object. It is therefore necessary in order to obtain visual and automatic interpretation of flaw size to recognize the continuous change in echo signal from a given size flaw as a function of its distance from the entering surface of the workpiece under test. This change in echo signal is non-linear and usually bidirectional. Thus, the response signal increases for a short distance in the workpiece (near field zone), reaches a peak (near field limit), and then continues to decrease throughout the remainder of the test piece, (far field).

This problem was recognized by Weighart as documented in his U.S. Pat. No. 3,033,029. This prior art patent describes a gain control system with complex wave shapes for the control voltage and discusses the result of the near field and far field effects of the beam geometry as well as the exponential attenuation with depth in the material. As shown in FIG. 1 of the Weighart patent, not only does the quantity of returned energy vary with distance within the test piece, but it varies nonlinearly as a complex function of distance (or time). The lower amplitude response for short distances is due to the near field effect. As illustrated in the Weighart patent, the signals first increase with distance below the surface and then decrease with distance below the surface.

Various prior art devices have sought to compensate for this effect by the use of distance amplitude compensation techniques, such as shown in Weighart, which change the gain of the receiver. Such devices have typically been referred to as distance amplitude compensation systems.

These conventional devices have sought to provide distance amplitude compensation by changing the gain of the receiver amplifier rapidly with each sweep trace, e.g., several dB in a few microseconds. Such devices are disclosed in *Radar Handbook*, by Skolnik, Ed., McGraw-Hill, New York, N.Y. There are several limitations and disadvantages to conventional distance amplitude compensation systems using the time-varied gain method. Very fast gain changes cannot be made easily because transients are introduced in the amplifier which produce false signals. The distance amplitude compensation function cannot be abruptly terminated at the start of the back reflection, which is ordinarily very large compared to flaw signals. This aggravates the problem of displaying the desired back echo on-screen when applying "back-echo gain" control. The linearity and/or dynamic range of the amplifier may be adversely affected by the distance amplitude compensation control using this time-varied-gain method.

Another problem with typical prior art systems relates to the set-up of such devices. Ordinarily, the operator must be provided with a distance amplitude response function curve which was previously obtained experimentally. Alternatively, the operator may be provided with a set of distance amplitude test blocks and be required to establish his own curve. If the effect of gain control function is not displayed on the CRT, the operator must use trial and error techniques to establish the echo signals from various depth blocks, an almost impossible task. In general, only one echo at a time from each block can be displayed. Even if the distance amplitude compensation control voltage can be displayed on the CRT, various trial and error adjustments of the several distance amplitude compensation controls must be made to compensate for the near field slope, far field slope, amplitude, and delay so that the desired gain effect may be obtained.

It can be shown that for the usual distance amplitude compensation method of receiver gain control, the voltage needed at the amplifier is a non-linear function of the distance amplitude response curve. If curve matching is used to set up the distance amplitude compensation system, a rather elaborate and very precise electronic method must be employed to present the inverse of the distance amplitude compensation control signal in both shape and absolute level referenced against the echo amplitude signals to be corrected. For curve matching, the distance amplitude compensation waveshape must be displayed on an alternate sweep trace in order not to be superimposed on the regular video trace. Display systems in which this is not done are especially difficult to use because there is inadequate CRT screen height to show large signals added to the distance amplitude compensation waveshape curve.

Various prior art devices use a flaw gate which produces an output of alarm when the echo amplitude in the gate portion of the time sweep rises above a selected level, as shown, for example, in U.S. pat. No. 2,883,860 to Henry. Such conventional devices use a rectangular gating function having a length corresponding to the material depth to be examined and a constant amplitude corresponding to the alarm level. The gating function of such devices has essentially constant sensitivity along its length and, to achieve automatic distance amplitude compensation, the receiver amplifier gain in such devices is controlled by distance amplitude compensation techniques as described above with the inherent pitfalls as set forth above.

SUMMARY

The present invention provides a distance amplitude compensation system for providing a comparison of a received signal with a reference signal have a time varying amplitude. To obtain this, the present invention provides a comparator circuit which compares received signals with the output waveshape of a distance amplitude compensation generator. If the amplitude of any of the received signals exceeds the time varying amplitude of the distance amplitude compensation generator, an alarm circuit is activated. The comparison between the received signals and the reference signal from the distance amplitude compensation generator may also be viewed on the screen of a CRT.

The present invention is particularly adapted to be used in an ultrasonic non-destructive testing system to provide an A scan presentation on a CRT screen to indicate the depth in a workpiece at which a flaw is located as well as the amplitude of the flaw signal. The invention may alternatively be used to provide a B scan presentation on a CRT screen to indicate the flaw depth in an object as well as the flaw distribution in cross sectional view. This application of the invention is particularly significant in medical testing of organs as well as non-destructive testing of inanimate workpieces. The present invention may also be used to provide C scan presentation on a cathode ray screen to indicate flaw distribution in a workpiece in plan view. A gated alarm system also provides an electrical signal for an alarm to indicate a flaw in the workpiece.

A pulser provides an initial signal through a suitable transducer to a workpiece or other object to be tested and a receiver receives echo signals and amplifies them. The gain of the receiver is constant and the output signals from the receiver remain a function of attenuation within the workpiece.

The attenuated received signals are transmitted to a comparator system. A distance amplitude compensation generator transmits a reference signal having a time varying amplitude to the comparator system and the received signals are compared with the reference signal by the comparator system. The comparator system includes alarm means for providing an alarm signal when any of the received signals exceeds the reference signal generated by the distance amplitude compensation generator.

The received signals and the reference signal are also transmitted during alternate portions of a clock pulse cycle to the screen of a cathode ray tube to display both the received signals and the reference signal. Although the received signals are displayed only during one half of the clock pulse cycle and the reference signal have a time varying amplitude, is displayed during the other half of the clock pulse cycle, the time period between the displaying of the received signals and the reference signals is so short that the eye of an observer discerns a composite display of both signals. The CRT thus produces a visual comparison of the received signals with the reference signal to determine whether the received signals exceed the reference signal thereby signaling a flaw or other discontinuity in the workpiece under test.

In the application of the present invention for nondestructive testing, the signal applied to the workpiece is an ultrasonic signal and the distance amplitude compensation generator is constructed using a suitable network of capacitors and resistors to provide an exponential rise corresponding to the near field and an exponential decay corresponding to the far field attenuation to provide a distance amplitude compensation reference signal. The reference signal is applied to the comparator which includes a threshold comparator system for transmitting TTL (transistor transistor logic) pulses to a gate which in turn enables an alarm latch if the received signals, which correspond to the echo signals from the ultrasonic test pulse, exceed the reference signal. The amplitude of the TTL pulses are equal, and the width of each pulse is determined by the width of the corresponding echo signal at the threshold level determined by the amplitude of the distance amplitude compensation reference signal.

The received signals as well as the reference signal are also applied to a vertical analog switch which is operative to transmit the received signals as well as the reference signal, during alternate portions of a clock pulse cycle, to the vertical amplifier of a suitable CRT. Unblanking circuit means is coupled to the CRT to enable it to display the receive signals corresponding to the echo signals from the workpiece, as well as the reference signal during alternate portions of the clock pulse cycle to provide a comparison between the received signals and the reference signal to enable an observer to determine whether the workpiece has any flaw or discontinuity, which produces an echo signal which exceeds the threshold determined by the reference signal.

It may be seen that although the received signal does continue to be a function of the attenuation of the pulse signal in the workpiece, the received signal is compared to an alarm level in the comparator and gate circuit which varies with time as a function of the attenuation. As a result, the actuation of the alarm can be made a direct function of the size of the discontinuity in the workpiece and independent of the attenuation of the pulse signal in the workpiece.

DRAWINGS

FIGS. 3A through 3N are timing diagrams of the present invention.

DESCRIPTION OF THE PREFERRED EMBODIMENT

Figure 1:
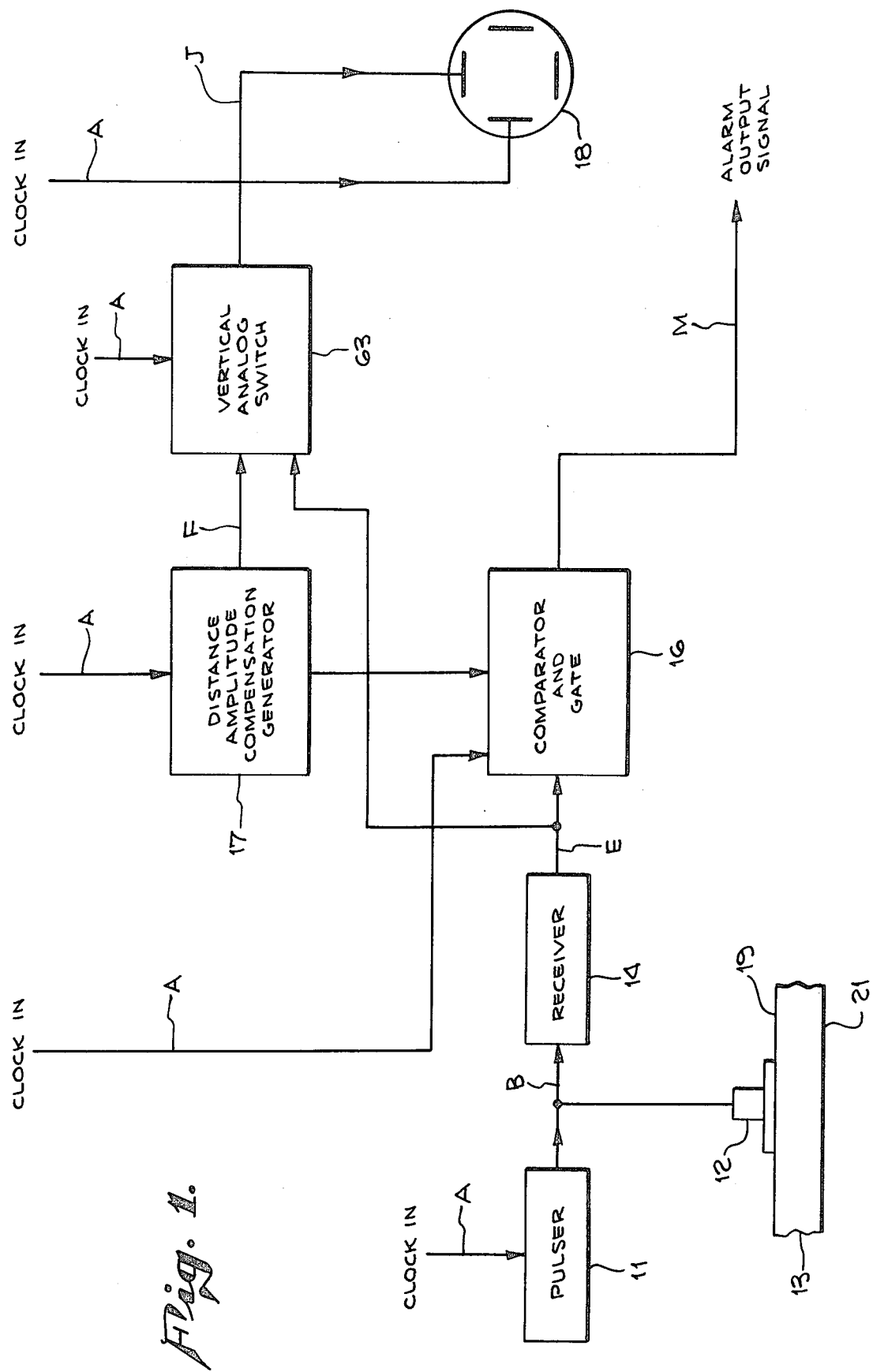
FIG. 1, is a basic block diagram of the present invention.

Referring to FIG. 1 there is shown the distance amplitude compensation system of the present invention having a pulser means 11 for transmitting an electric wavetrain to a transducer 12 which generates ultrasonic signals which are transmitted to a workpiece 13. The echo signals are received by the transducer 12 and transmitted to a receiver means shown as receiver 14 which converts the signals to video signals.

The video signals are transmitted to a comparator and gate circuit 16 and a distance amplitude compensation signal generator means 17 tramsmits a reference signal having a time varying amplitude to the comparator and gate circuit 16. If the receivec signals, which correspond to echo signals from the workpiece 13, exceed the time varying amplitude of the reference signal generated by the distance amplitude compensation generator 17, an alarm signal is generated by the alarm output of the comparator and gate circuit 16. The output of the distance amplitude compensation generator 17 and the output of the receiver 14 are also coupled to vertical analog switch means 63 which is clocked to transmit the reference signal and the received signals during different portions of the clock pulse cycle to a suitable CRT 18 for displaying the received signals as well as the reference signals on the screen of the CRT.

blanking pulse shown in FIG. 3G for a predetermined period of time. The gate pulse generating circuit 61 includes suitable delay circuitry and the duration of the delay may be controlled by any standard control mechanism.

The output rectangular pulse from the gate pulse generating means 61, shown in FIG. 3G is also fed to the second input of AND gate 58 to thereby enable the AND gate 58 to pass the TTL pulses, shown in FIG. 3K during the duration of the pulse shown in FIG. 3G. The output of AND gate 58 is therefore a train of TTL pulses shown in FIG. 3L which is fed through an alarm latch 62 which may be coupled to any suitable alarm signaling device to provide an alarm output signal. The alarm output signal may be in the form of an audible signal for a predetermined period of time which audibly informs the operator that a flaw or discontinuity has been detected. Alternatively, the alarm output signal may be coupled to any mechanical or electronic utilization device to record the detection of the flaw or discontinuity.

The output of the alarm level control 56 also feeds the output waveform from the distance amplitude compensation generator, shown in FIG. 3F to vertical switch means shown as a vertical analog switch 63. The output of the receiver 14 is also fed to a second input of the vertical analog switch 63 and the output of the vertical analog switch 63 produces video signals during the main half of the clock pulse cycle and a distance amplitude compensation waveform during the alternative half of the clock pulse cycle as shown in FIG. 3H. The vertical analog switch 63 as well as the unblanking analog switch 53 preserve the amplitude of the input signal and permit the transmission thereof when activated. The analog switches are known in the art and may be formed, for example, of a suitable configuration of field effect transistors (FET's).

The output of the vertical analog switch 63 shown in FIG. 3H is fed to a vertical amplifier 64 which controls the vertical deflection of the trace on the CRT 18. As indicated above, the horizontal deflection is obtained by the horizontal amplifier 52 which in turn, is controlled by the sweep and unblanking generator 51 to produce the signal shown in FIG. 3C. The CRT 18 is activated by the unblanking amplifier 54 which, in turn, is controlled by the unblanking analog switch 53 for a period of time as shown in the waveform of FIG. 3I. The CRT 18 therefore displays both the video signals as well as the distance amplitude compensation waveform to provide a visual comparison between the echo signals received by the receiver 14 with the distance amplitude compensation reference signal.

The width of the distance amplitude compensation waveform displayed on the screen of the CRT 18 is therefore controlled by the width of the pulse generated by the gate pulse generator 61 during the alternate half of the clock pulse generator as shown in FIG. 3G. The width of the pulse shown in FIG. 3G during the alternate half of the clock pulse cycle corresponds to the locations of the gated area with respect to the distance between the front and rear surfaces of the workpiece. Thus the width of the distance amplitude compensation waveform also corresponds to the depth of the gated portion of the workpiece.

The video signals received by the receiver 14, which correspond to the echo pulses received by the transducer 12, are displayed on the screen of the CRT 18 during the main portion of the clock pulse cycle shown in FIG. 3A. The distance amplitude compensation waveform, shown in FIG. 3F and generated by the distance amplitude compensation generator 17 is displayed on the screen of the CRT 18 during the alternate half of the clock pulse cycle shown in FIG. 3A. This alternate display on the video signals during the first, or main, half of the clock pulse cycle and the distance amplitude compensation waveform displayed during the second, or alternate half of the clock pulse cycle occurs so rapidly that the eye of a human viewer discerns a composite picture of the video signals and the distance amplitude compensation waveform as shown in FIG. 3N. When the video signal shown in FIG. 3N exceeds the distance amplitude compensation waveform, the viewer is visually informed that a flaw or discontinuity has been detected in the object, such as workpiece 13, under test.

The clock pulse generator provides clock pulses having main and alternate portions each having opposite states as shown in FIG. 3A. During the main half of the clock pulse cycle shown in FIG. 3A, the pulser 11 generates a pulse which, in the preferred embodiment, is in the order of 1 microsecond in duration, and the sweep and unblanking generator 51 generates a sweep signal shown in FIG. 3C and a main unblanking rectangular wave, 3D, during the alternate half of the clock pulse cycle in the same manner that these pulses are generated during the main half of the clock pulse cycle. Since the pulse signal shown in FIG. 3B is generated at the beginning of both the main and alternate halves of the clock pulse cycle, the echo signals are received and converted to video signals shown in FIG. 3E during both halves of the clock pulse cycle.

The distance amplitude compensation waveform shown in FIG. 3F and generated, as described above, by the distance amplitude compensation generator 17 is also produced at the beginning of both the main and alternate halves of the clock pulse cycle.

The vertical analog switch 63 transmits the video pulses during the main half of the clock pulse cycle and the distance amplitude compensation waveform during the alternate half of the clock pulse cycle as shown in FIG. 3H. This is achieved by the transmission of the signal on the video input shown in FIG. 3E during the main half of the clock pulse cycle and the blocking off of the channel from the distance amplitude compensation generator to prevent the waveform shown in FIG. 3F to be transmitted during the main half of the clock pulse cycle. Correspondingly, during the alternate half of the clock pulse cycle, the video input, FIG. 3E, is not transmitted and the distance amplitude compensation generator waveform, FIG. 3F, is transmitted.

The clock pulse signal, FIG. 3A, is also supplied to the unblanking analog switch 53 and during the main half of the clock pulse cycle, output of the main unblanking input terminal is transmitted to provide an output signal of the unblanking analog switch 53 shown in FIG. 3I having a time duration determined by the time duration of the main unblanking pulse shown in FIG. 3D during the main half of the clock pulse cycle. The input signal to the unblanking analog switch 53 from the gate pulse generator 61 is not transmitted during this main half of the clock pulse cycle. Correspondingly, during the alternate half of the clock pulse cycle, the signal from the sweep and unblanking generator 51 having a waveform shown in FIG. 3D, is not transmitted, and the input from the gate pulse generator 61

Although the present invention may be utilized in a wide variety of applications, it is particularly adapted to be embodied in an ultrasonic nondestructive testing system for inspecting the internal structures of various types of workpieces 13. The pulses from the pulser 11, shown in FIG. 3B, are acoustically coupled to the workpiece 13 by a suitable transducer 12 which preferably includes a piezoelectric crystal which produces acoustical signals which are transmitted through the front surface 19 of the workpiece and are propagated through the workpiece. Echoes of the ultrasonic pulses are reflected from any discontinuities in the workpiece 13 such as holes, openings, cracks, inclusions, fissures and flaws. In addition, if any of the energy reaches the rear surface 21 of the workpiece, it is reflected. At least a portion of the propagated signals are returned as echo signals to the transducer 12 and are amplified by the receiver 14 which includes a constant gain amplifier.

The receiver 14 has a constant gain and provides an output of video signals as shown in FIG. 3E which correspond to the echo signals received by the transducer 12. As shown in FIG. 3E the echo signals normally include a pulse 30 corresponding to the front surface 19 of the workpiece 13. This is followed at some later point of time by another pulse 40 which corresponds to the back surface 21 of the workpiece 13. The time delay between these two pulses 30 and 40 corresponds to the time required for the ultrasonic energy generated by the transducer 12 to propagate from the front surface 19 through the workpiece 13 and to the rear surface 26 and return to the front surface 19.

If there are one or more discontinuities inside the workpiece 13, there would be a corresponding number of pulses 32, 34, 36 and 38 as shown in FIG. 3E between the front pulse 30 and the rear pulse 40. The time delay for the individual pulses is the function of the distance to the reflecting discontinuity.

The magnitudes of each of the echo pulses and, correspondingly each video pulse 30 through 40, is a function of the apparent size of the associated reflecting discontinuities. However, the magnitude of the received pulse is also a function of whether the discontinuity is in the near field zone or the far field zone.

In the near field zone, the ultrasonic energy tends to converge toward a focal point. In the far field zone beyond the focal point, the energy tends to diverge. As a result, if a given size discontinuity is situated in the near field zone, as it recedes from the tranducer 12 toward the focal point, the energy tends to concentrate and therefore the pulse tends to increase. As the same discontinuity recedes beyond the focal point, the energy diverges and the pulse decreases. In this zone, the pulse tends to decrease as an exponential function of time so that the pulse is a function of the distance of the discontinuity in the workpiece from the transducer.

Figure 2:
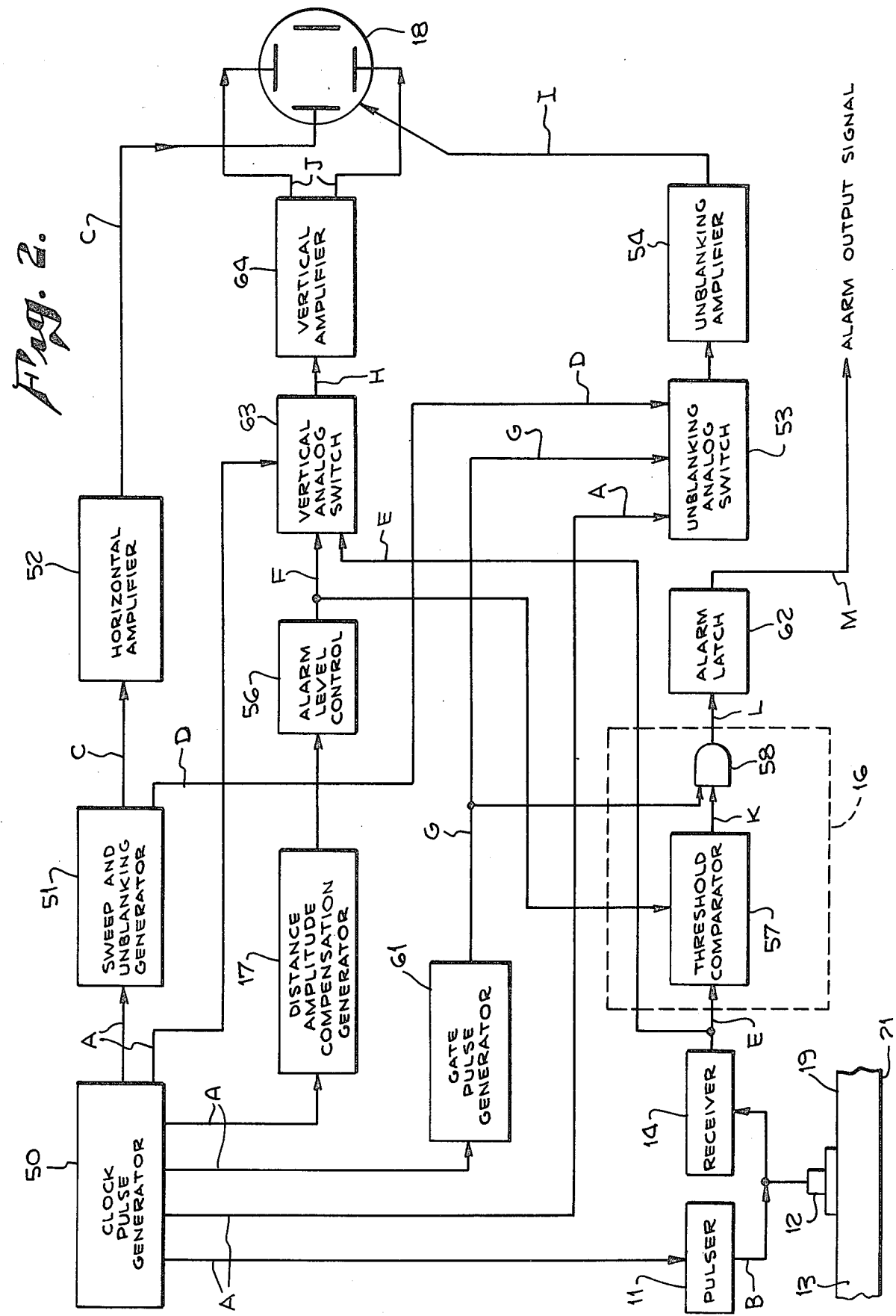
FIG. 2, is a detailed block diagram of the present invention.

As shown in FIG. 2, the entire distance amplitude compensation system is synchronized by clock pulses generated by a clock pulse generator 50 which produces clock pulses as shown in FIG. 3A. By way of example, the frequency of the clock pulse generator may vary between 100 hertz to 10 kilohertz. However, for most applications, the clock pulse generator 50 will operate at a frequency in the order of 1 kilohertz.

The clock pulse is transmitted to the pulser 11 which generates a pulse shown in FIG. 3B which is transmitted to the transducer 12 to convert the pulse to ultrasonic energy which is propagated into the workpiece 13 as described above. The echo pulses received by the transducer 12 are fed to the receiver 14 which includes a constant gain amplifier circuit and is operative to convert the received echo pulses to video signals as shown in FIG. 3E. The clock pulse A is also transmitted to the distance amplitude compensation waveform generator 17 as shown in FIG. 2.

The distance amplitude compensation generator provides a waveform as shown in FIG. 3F which is shaped to accommodate the change in amplitude of the echo signal in the workpiece due to the near field zone effect and the far field zone effect. The wave shape shown in FIG. 3F may be generated by charging and discharging capacitors through adjustable networks to provide the exponential rise and decay. This signal may be provided by circuits such as that shown in U.S. Pat. No. 3,033,029 to Weighart.

The clock pulse generator 50 also couples a clock pulse to unblanking generator means shown as a sweep and unblanking generator 51 as shown in FIG. 2. The sweep and unblanking generator 51 is a standard sweep generator and provides a saw-tooth wave as shown in FIG. 3C to a horizontal amplifier 52 which is coupled to the horizontal control plates of a standard CRT 18. A second output of the sweep and unblanking generator 51 provides a rectangular pulse signal as shown in FIG. 3D which is fed to unblanking switch means shown as an unblanking analog switch 53. The unblanking analog switch 53 is in turn coupled to an unblanking amplifier 54 which controls the intensity modulation of CRT 18 to enable it when the unblanking amplifier is activated.

Thus, the sweep and unblanking generator 51 is operative to generate a sweep signal as shown in FIG. 3C to control the horizontal trace of the CRT 18 for the time duration of the sweep signal. The rectangular pulse generated by the sweep and unblanking generator 51 as shown in FIG. 3D effectively turns on the CRT to enable the trace to appear for the duration of the unblanking pulse shown in FIG. 3D.

The output of the distance amplitude compensation generator 17 is fed to an alarm level control 56 which is a level shifter for shifting the DC level of the waveform shown in FIG. 3F.

The shifted waveform is applied to one input of a threshold comparator means 57. The video signals shown in FIG. 3E and received from a receiver 14 are fed to a second input of the threshold comparator 57. The threshold comparator 57 is a comparator circuit which generates pulses which have a fixed amplitude but a width and position which correspond to the video signals 3E that exceed the threshold determined by the output waveform 3F that is fed to the alarm threshold comparator 57.

The output pulses from the threshold comparator 57, shown in FIG. 3K are referred to as TTL (transistor transistor logic) video pulses and are fed to one input of an AND gate 58. The other input is from gate pulse generating means 61 for generating a gate pulse commencing at a predetermined point of time and having a predetermined time duration. Such devices are well known in the art and may be formed of suitable gate having delays for initiating a gate pulse at a predetermined point of time after the beginning of the clock pulse and terminating the gate pulse at a subsequent predetermined point of time. The gate pulse generating means 61 receives the clock pulse from the clock pulse generator 50 and delays the initiation of a gate pulse for a selectable predetermined period of time. The output of the gate pulse generating means 61 provides an unhaving a waveform shown in FIG. 3G is transmitted. Thus, the waveform shown in FIG. 3I is produced.

The alternate transmission of the two inputs of the unblanking analog switch 53 and the vertical analog switch 63 is achieved by means well known in the art. It may be achieved, for example, by coupling two FET's each to one of the circuit inputs and coupling their outputs together. The clock pulse generator is coupled to each of the two FET's in such a manner so as to transmit the input to one during the main half of the clock pulse cycle and transmit the signal to the second FET during the alternate half of the clock pulse cycle.

Since, as indicated above, the CRT 18 is enabled for the duration of the pulses shown in FIG. 3I, during the first half of the clock pulse cycle, the CRT displays the video signals received during the time duration of the main unblanking pulse of FIG. 3D, shown during the main half of the clock pulse cycle of FIG. 3I. During the alternate half of the clock pulse cycle, the CRT displays the distance amplitude compensation waveform generated during the alternate half of the clock pulse, shown in FIG. 3G, for the time duration of the unblanking pulse generated by the gate pulse generating means 61 as shown in FIG. 3I. As a result, the CRT screen 18 produces the signals shown in FIG. 3J with the video signals displayed during the main half of the clock pulse cycle and the distance amplitude compensation waveform displayed during the alternate half of the clock pulse cycle. The width of the distance amplitude compensation waveform displayed on the screen of the CRT 18 is therefore controlled by the width of the gate pulse generator so that the width of the display waveform corresponds to the location of the gated area with respect to the top and bottom surfaces 18 of the workpiece. As indicated above, since the time duration between the main and the alternate half of the clock pulses are relatively small, the human eye discerns a composite waveform of video signals and a distance amplitude compensation waveform such as that shown in FIG. 3N.

Thus, the present invention provides circuit means having an alarm threshold which can be varied in time in a selectable manner for providing an alarm signal when the echo signals exceed the alarm threshold. The AND gate 58 enables the operations of the circuit means for predetermined time durations shown in FIG. 3G. It is seen that although the AND gate 58 is shown coupled between the threshold comparator 57 and the alarm latch 62 in the preferred embodiment, the AND gate may be alternatively coupled between the receiver 14 and the threshold comparator 57.

Obviously, many modifications and variations of the present invention are possible in light of the above teachings. It is therefore to be understood that within the scope of the appended claims, the invention can be practiced otherwise than as specifically described.

I claim:

1. A distance amplitude compensation system for comparing signals transmitted through a workpiece with a reference signal having a time varying amplitude, said system including:
   receiver means for receiving said transmitted signals and converting them to video signals and having an output circuit,
   distance amplitude compensation signal generator means for generating a reference signal having a time varying amplitude for compensating for the variation of said transmitted signals in the workpiece, and having an output circuit, and
   comparator means having an input circuit coupled to the output circuit of said receiver means and an input circuit coupled to the output circuit of said distance amplitude compensation generator for comparting said video signals with said reference signal.

2. The system as defined in claim 1 and wherein said comparator means includes alarm threshold comparator means for producing a train of pulses each of said train corresponds to any of said video signals which has an amplitude which exceeds the threshold of said reference signal, each pulse of said train of pulses being equal in amplitude and having a width which varies in proportion to the width of the associated video signal at the threshold amplitude level of said reference signal, said alarm threshold comparator means having an output circuit.

3. The system defined in claim 2 and further including alarm output signalling means having an input circuit coupled to the output circuit of said alarm threshold comparator means for providing an alarm output signal in response to said train of pulses.

4. The system as defined in claim 2 and further including:
   gate pulse generating means for generating a gate pulse commencing at a predetermined point of time and having a predetermined time duration, said gate pulse generating means having an output circuit.
   AND gate means having a first input circuit coupled to the output circuit of said gate pulse generator means and a second input circuit coupled to the output circuit of said comparator means, and
   alarm latch means having an input circuit coupled to the output circuit of said AND gate means for providing an alarm output signal,
   whereby the transmission of said train of pulses to said AND gate during the application of said gate pulse energizes said alarm latch means to provide the alarm output signal.

5. The system as defined in claim 1 and further including a utilization device having an input circuit coupled to the output circuits of said receiver means and said distance amplitude compensation signal generator means for providing a visual display of the comparison of said video signals with said signal having a time varying amplitude.

6. The system as defined in claim 5 and wherein said utilization device including a cathode ray tube having a screen and a control circuit, and
   vertical switch means having a first input circuit coupled to the output circuit of said distance amplitude compensation generator means and a second input circuit coupled to the output circuit of said receiver means, and having an output circuit coupled to the control circuit of said cathode ray tube to control the vertical trace on the screen to transmit said video signals and said reference signal to said cathode ray tube to be displayed on the screen.

7. The system as defined in claim 6 and further including unblanking switch means coupled to said cathode ray tube for unblanking said cathode ray tube for predetermined time periods to display said video signals and said reference signal.

8. The system as defined in claim 7 and further including gate pulse generating means coupled to the input circuit of said unblanking switch means for generating a gate pulse commencing at a predetermined point of time and having a predetermined period of time for controlling said unblanking switch means for unblanking said cathode ray tube and displaying said reference signal for said predetermined period of time.

9. The system as defined in claim 6 and further including;
clock pulse generator means coupled to said vertical switch means and said unblanking switch means, said clock pulse generator means being operative to generate a train of clock pulses, each of which has a main portion having one polarity and an alternate portion having a second polarity,
whereby said vertical switch is energized to transmit said video signals to said cathode ray tube during said main portion of said clock pulse and to transmit said reference signal having a time varying amplitude to said cathode ray tube during said alternate portion of said clock pulse.

10. A system for comparing received signals corresponding to energy received from an object with a reference signal having a time varying amplitude comprising:
means for transmitting ultrasonic energy into the object,
receiver means for receiving said ultrasonic energy after it has propagated through the object, said receiver means being effective to produce a received signal corresponding to said energy received from the object,
signal generator means adapted to produce a reference signal having a time varying amplitude corresponding to the variations in the ultrasonic energy as it propagates through the object, and
signal comparator means coupled to said receiver means and said signal generator means for comparing the receiving and reference signals with each other.

11. An ultrasonic non-destructive testing system for inspecting an object, said system including the combination of
clock pulse generator means for producing a series of timing pulses,
transmitting means coupled to said clock pulse generator means for transmitting pulses of ultrasonic energy into the object synchronously with said timing pulses, said ultrasonic energy being effective to propagate through said object whereby echoes thereof are reflected from discontinuities, with the time and the magnitude of each echo being a function of the distance to the discontinuity and the size of the discontinuity,
receiver means for receiving said echoes and producing a signal having a time and magnitude corresponding to the echoes,
signal generator means coupled to said clock pulse means for producing a reference signal having a time varying amplitude which is synchronized with said timing pulses,
comparator means coupled to said receiver means and said signal generator means, said comparator means being effective to compare the received signal and the reference signal, and
a utilization device coupled to said signal comparator and effective to produce a signal when the received signal exceeds the reference signal.

12. An ultrasonic non-destructive testing system for inspecting a workpiece, said system including the combination of:
pulser means for repeatedly transmitting pulses of ultrasonic energy to a workpiece, said pulses of energy being effective to propagate through said workpiece whereby echoes of said pulses are reflected from discontinuities therein,
receiver means for receiving the echoes returned from the workpiece and producing a received signal corresponding to the received energy, whereby the magnitude of the signal is a function of the size of the discontinuity and its depth in the material,
signal generator means adapted to produce a reference signal that varies as a function of time corresponding to the variation of said ultrasonic energy as it propagates through the workpiece,
a cathode ray tube for producing a visual display of a signal,
means for alternately coupling said receiver means and said signal generator means to said cathode ray tube for producing superimposed displays of the received signal and the reference signal, and
a signal comparator coupled to said receiver means and said signal generator, said comparator means being effective to compare said received signal with the reference signal and produce an alarm signal when the received signal exceeds the reference signal.

13. The ultrasonic nondestructive testing system of claim 12 further including:
clock pulse generator means coupled to said signal generator means and said pulser means to produce clock pulses to synchronize the operation of said signal generator means with the operation of said pulser means.

14. The ultrasonic nondestructive testing system of claim 12 and further including:
clock pulse generator means coupled to said means for alternately coupling said receiver means and said signal generator means to said cathode ray tube for producing superimposed displays of the received signal and the reference signal on said cathode ray tube.

15. A method for comparing received signals corresponding to ultrasonic energy received from a workpiece being tested with a reference signal including the steps of:
transmitting ultrasonic energy into the workpiece under test;
receiving the ultrasonic energy after it has propagated through the workpiece;
converting the received ultrasonic energy after it has propagated through the workpiece into an electrical signal;
generating a reference signal having a time varying amplitude corresponding to variations in the ultrasonic energy as it propagates through the workpiece; and
comparing the received electrical signal with the reference signal.

16. The method as defined in claim 15 and further including the step of producing an alarm signal when the received electrical signal exceeds the reference signal.

17. The method as defined in claim 16 and further including the step of displaying the reference signal and the received electrical signal on the screen of a cathode ray tube.

* * * * *